(12) United States Patent
Van Vliet et al.

(10) Patent No.: US 8,871,985 B2
(45) Date of Patent: Oct. 28, 2014

(54) PROCESSES FOR THE PRODUCTION OF ALCOHOLS

(75) Inventors: Arie Van Vliet, Sterrebeek (BE); Eddy T. Van Driessche, Eeklo (BE)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/579,447

(22) PCT Filed: Jan. 19, 2011

(86) PCT No.: PCT/US2011/021616
§ 371 (c)(1),
(2), (4) Date: Oct. 18, 2012

(87) PCT Pub. No.: WO2011/115695
PCT Pub. Date: Sep. 22, 2011

(65) Prior Publication Data
US 2013/0109890 A1 May 2, 2013

Related U.S. Application Data

(60) Provisional application No. 61/313,946, filed on Mar. 15, 2010.

(30) Foreign Application Priority Data

Apr. 23, 2010 (EP) .................................... 10160909

(51) Int. Cl.
| | | |
|---|---|---|
| C07C 29/16 | (2006.01) | |
| C07C 29/141 | (2006.01) | |
| C07C 29/17 | (2006.01) | |
| C07C 45/50 | (2006.01) | |
| C07C 31/125 | (2006.01) | |
| C07C 47/02 | (2006.01) | |

(52) U.S. Cl.
CPC ............... *C07C 29/141* (2013.01); *C07C 29/16* (2013.01); *C07C 29/175* (2013.01); *C07C 45/50* (2013.01)
USPC ........................... 568/882; 568/451; 568/885

(58) Field of Classification Search
None
See application file for complete search history.

(56) References Cited

U.S. PATENT DOCUMENTS

| | | |
|---|---|---|
| 2,809,220 A | 10/1957 | Mertzweiller et al. |
| 4,401,834 A | 8/1983 | King |

(Continued)

FOREIGN PATENT DOCUMENTS

| | | |
|---|---|---|
| DE | 2628987 | 1/1978 |
| DE | 19842370 | 3/2000 |

(Continued)

OTHER PUBLICATIONS

Jenner, G. et al. J. Mol. Catal. 1991, 64, 337-347.*
Jenner, G. "Catalytic procedure for the synthesis of cyclohexanemethanols from cycloalkenes and aqueous methyl formate" Tetrahedron Lett. 1991, 32, pp. 505-508.*

* cited by examiner

*Primary Examiner* — Jafar Parsa
*Assistant Examiner* — Medhanit Bahta
(74) *Attorney, Agent, or Firm* — Leandro Arechederra, III; Luke A. Parsons

(57) ABSTRACT

The disclosure generally relates to a process for the production of a $C_6$-$C_{15}$ alcohol mixture including the steps of hydroformylating an olefin mixture including at least one branched $C_5$-$C_{14}$ olefin to form a hydroformylation product including aldehydes and formates; feeding the hydroformylation product into a hydrogenation step including contacting, in at least one first hydrogenation reactor, at least one catalyst, water, hydrogen, and the hydroformylation product to convert the hydroformylation product to a $C_6$-$C_{15}$ alcohol mixture; wherein the hydrogen is supplied from the decomposition of the formates and at least one source external to the at least one first hydrogenation reactor.

24 Claims, 3 Drawing Sheets

Formates Contribution to Hydrogen Excess for Aldehyde Hydrogenation

(56) References Cited

U.S. PATENT DOCUMENTS

| | | |
|---|---|---|
| 5,059,710 A | 10/1991 | Abatjoglou et al. |
| 5,306,848 A | 4/1994 | Vargas |
| 6,239,318 B1 | 5/2001 | Schuler et al. |
| 6,680,414 B2 * | 1/2004 | Knoop et al. ............ 568/830 |
| 7,405,329 B2 * | 7/2008 | Beadle et al. ............ 568/451 |
| 8,143,459 B2 * | 3/2012 | Van Driessche et al. .... 568/899 |
| 8,288,595 B2 * | 10/2012 | Van Driessche et al. .... 568/899 |
| 2007/0161829 A1 * | 7/2007 | Van Driessche ............ 568/883 |
| 2012/0149935 A1 | 6/2012 | Van Driessche et al. |

FOREIGN PATENT DOCUMENTS

| | | |
|---|---|---|
| DE | 10241266 | 3/2004 |
| EP | 0319208 | 4/1992 |
| GB | 1579159 | 11/1980 |
| GB | 2142010 | 1/1985 |
| WO | WO01/97809 | 12/2001 |
| WO | WO2005/058782 | 6/2005 |

PROCESSES FOR THE PRODUCTION OF ALCOHOLS

CROSS REFERENCE TO RELATED APPLICATIONS

This patent application is a National Stage Application of International Application No. PCT/US2011/021616 filed Jan. 19, 2011, which claims the benefit of U.S. Ser. No. 61/313,946, filed Mar. 15, 2010, and EP 10160909.7, filed Apr. 23, 2010, the disclosure of which is incorporated by reference in its entirety.

This application is also related to U.S. Ser. No. 61/183,575, filed Jun. 3, 2009.

FIELD OF THE INVENTION

The invention relates to processes for the hydrogenation of aldehydes or aldehyde mixtures for the production of alcohols or alcohol mixtures.

BACKGROUND

Alcohols may be obtained by catalytic hydrogenation of aldehydes which have been obtained, for example, by hydroformylation of olefins, often referred to as the oxo or oxonation process or oxo synthesis. Large quantities of alcohols are used as solvents and as intermediates for preparing many organic compounds. Important downstream products of alcohols are plasticizers and detergents.

Aldehydes may be catalytically reduced with hydrogen to form alcohols. Catalysts which include at least one metal of groups 1b, 2b, 6b, 7b and/or 8 of the Periodic Table of the Elements are frequently used. The hydrogenation of aldehydes may be carried out continuously or batchwise using catalysts in the gas or liquid phase.

For example, U.S. Pat. No. 6,680,414 (equivalent to EP 1 219 584 B) discloses a process comprising in a homogeneous liquid phase comprising water, and over a fixed-bed catalyst, continuously hydrogenating at least one hydroformylation product obtained directly from a hydroformylation of one or more $C_{4-16}$ olefins to produce at least one output mixture: wherein said fixed-bed catalyst comprises at least one element of transition group eight of the Periodic Table of the Elements; wherein said output mixture comprises at least one corresponding alcohol and from 0.05 to 10% by weight of water; and wherein in a steady-state operation of the process, from 3 to 50% more hydrogen is fed to the hydrogenation than is consumed by the hydrogenation.

Other background references include GB 2 142 010, DE 198 42 370, DE 2 628 987, DE 198 42 370, DE 102 41 266, WO 2001/97809, WO 2005/058782, EP 3 192 08 A, U.S. Pat. Nos. 2,809,220, 4,401,834, 5,059,710, and 5,306,848.

For the industrial production of alcohols by hydrogenation of aldehydes from the oxo process, preference is given, especially in the case of large-volume products, to continuous gas or liquid phase processes using catalysts located in a fixed bed.

Compared to gas-phase hydrogenation, liquid-phase hydrogenation has a more favorable energy balance and gives a higher space-time yield. As the molar mass of the aldehyde to be hydrogenated increases, i.e., as the boiling point increases, the advantage of the more favorable energy balance increases. Higher aldehydes having more than 6 carbon atoms, preferably, from 6 to 15 carbon atoms, are hydrogenated in the liquid phase.

However, hydrogenation in the liquid phase has the disadvantage that, owing to the high concentrations of both aldehydes and alcohols, the formation of what U.S. Pat. No. 6,680,414, terms "high boilers" via subsequent and secondary reactions is promoted. Thus, aldehydes can more readily undergo aldol reactions (addition and/or condensation) and form hemiacetals or acetals with alcohols. The acetals or hemiacetals formed can undergo elimination of alcohol or water, respectively, to form (unsaturated) ethers which are hydrogenated under the reaction conditions to form saturated ethers. These secondary by products thus reduce the yield. Industrial aldehyde mixtures which are used for the hydrogenation frequently already contain varying concentrations of "high boilers."

For example, hydroformylation of olefins in the presence of cobalt catalysts gives crude aldehydes which contain esters of formic acid (formates) and also aldol products, high esters, and ethers as well as acetals as "high boilers."

For some commercial processes utilizing a hydroformylated product as a raw starting material, the hydrogenation feed, i.e., the feed to be hydrogenated, may contain up to 15 wt % of formates. When in contact with the hydrogenation catalyst, for example, copper chromite, sulphided nickel, moly catalyst, or nickel catalyst, the formates decompose to form the oxo alcohol, $CH_3OH$ (methanol), $H_2$ (hydrogen), and $CO_2$ (carbon dioxide). Methanol formation is favored when the water content of the hydrogenation feed is low and the reactor temperature and pressure are high. Alternatively, $CO_2$ and $H_2$ formation is favored when the water content of the reactor is close to 3 wt % and the temperature and pressure of the reactor are on the low side, for example, from 100-200° C. at 10-60 bar. The hydrogen generated from the decomposition may be useful for the hydrogenation reaction of aldehydes under certain conditions. However, the production of too much methanol is undesirable because it may end up in plant waste water. The following reaction schedules are also provided for further illustration.

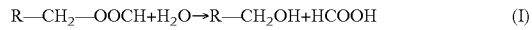
$$R-CH_2-OOCH+H_2O \rightarrow R-CH_2OH+HCOOH \quad (I)$$

$$HCOOH \rightarrow CO_2+H_2 \quad (II)$$

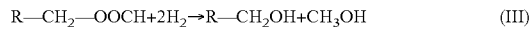
$$R-CH_2-OOCH+2H_2 \rightarrow R-CH_2OH+CH_3OH \quad (III)$$

Additionally, without being bound to theory, the methanol may promote the formation of by products such as methyl nonanoate by an esterification reaction with nonanoic acid which is present in the hydrogenation feed.

Thus, there exists the need to provide a hydrogenation process that utilizes hydrogen produced from the decomposition of formates while minimizing the amount methanol and its resulting by products also produced from the same decomposition or from subsequent reactions.

SUMMARY

The invention provides for a process for the production of a $C_6$-$C_{15}$ alcohol mixture comprising the steps of: hydroformylating an olefin mixture comprising at least one branched $C_5$-$C_{14}$ olefin to form a hydroformylation product comprising aldehydes and formates; feeding the hydroformylation product into a hydrogenation step comprising contacting, in at least one first hydrogenation reactor, at least one catalyst, at least 1 wt % water, based upon the total weight of the feed, hydrogen, and the hydroformylation product to convert the hydroformylation product to a $C_6$-$C_{15}$ alcohol mixture; wherein the hydrogen is supplied from the decomposition of the formates and at least one source external to the at least one first hydrogenation reactor, and wherein at least 5% or greater of the total stoichiometric amount of hydrogen necessary to hydrogenate the aldehydes is supplied from the decomposition of the formates and 100% or less than 100% of the total stoichiometric of hydrogen necessary to hydrogenate the aldehydes is supplied from the at least one source external.

In any of the embodiments disclosed herein, at least 10% or greater of the total stoichiometric amount of hydrogen necessary to hydrogenate the aldehydes may be supplied from the decomposition of the formates.

In any of the embodiments disclosed herein, at least 15% or greater of the total stoichiometric amount of hydrogen necessary to hydrogenate the aldehydes may be supplied from the decomposition of the formates.

In any of the embodiments disclosed herein, at least 25% or greater of the total stoichiometric amount of hydrogen necessary to hydrogenate the aldehydes may be supplied from the decomposition of the formates.

In any of the embodiments disclosed herein, at least 30% or greater of the total stoichiometric amount of hydrogen necessary to hydrogenate the aldehydes may be supplied from the decomposition of the formates.

In any of the embodiments disclosed herein, the hydrogen supplied from the decomposition of the formates and the at least one source external to the at least one first hydrogenation reactor may be supplied in an excess of from 10-100% of the total stoichiometric amount of hydrogen necessary to hydrogenate the aldehydes.

In any of the embodiments disclosed herein, the hydrogen supplied from the decomposition of the formates and the at least one source external to the at least one first hydrogenation reactor may be supplied in an excess of from 10-50% of the total stoichiometric amount of hydrogen necessary to hydrogenate the aldehydes.

In any of the embodiments disclosed herein, the hydrogen supplied from the decomposition of the formates and the at least one source external to the at least one first hydrogenation reactor may be supplied in an excess of from 10-40% of the total stoichiometric amount of hydrogen necessary to hydrogenate the aldehydes.

In any of the embodiments disclosed herein, the hydrogen supplied from the decomposition of the formates and the at least one source external to the at least one first hydrogenation reactor may be supplied in an excess of from 30-50% of the total stoichiometric amount of hydrogen necessary to hydrogenate the aldehydes.

DETAILED DESCRIPTION

Figure 1:
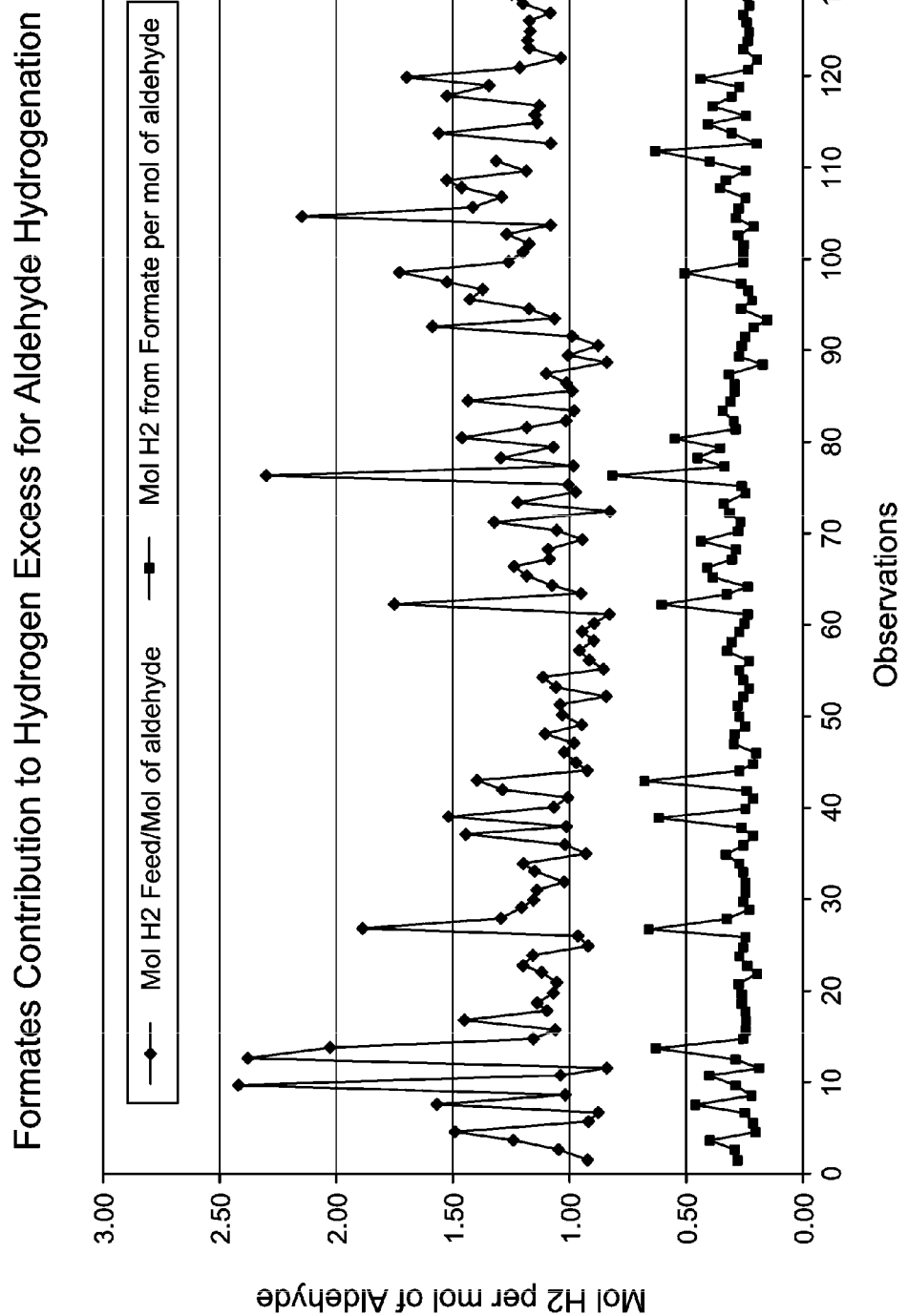
FIG. 1 is a graph showing the amount of hydrogen contributed from the decomposition of formates during the hydrogenation of a hydroformylated product comprising aldehydes.

As used herein, all reference to the Periodic Table of the Elements and groups thereof is to the NEW NOTATION published in HAWLEY'S CONDENSED CHEMICAL DICTIONARY, Thirteenth Edition, John Wiley & Sons, Inc., (1997) (reproduced therewith permission from IUPAC), unless reference is made to the Previous IUPAC form denoted with Roman numerals (also appearing in the same), or unless otherwise noted.

Alcohols may be obtained by catalytic hydrogenation of aldehydes or aldehyde mixtures that have been obtained, for example, by hydroformylation of olefins. As used herein, "aldehyde mixture" refers to any mixture comprising at least 1 wt % or more of at least one aldehyde, based upon the total weight of the feed into the hydrogenation process. In some embodiments, the amount of aldehyde in the feed to the reactor may be from 1-60 wt %, alternatively, 5-20 wt %, based upon the total weight of the feed.

Starting Materials: Olefins

The starting materials for the preparation of the aldehydes or aldehyde mixture by hydroformylation are olefins or mixtures of olefins having generally from 4 to 16, preferably from 6 to 15, carbon atoms and either terminal or internal C—C double bonds, e.g., 1-butene, 2-butene, isobutene, 1- or 2-pentene, 2-methyl-1-butene, 2 methyl-2-butene, 3-methyl-1-butene, 1-, 2- or 3-hexene, the $C_6$-olefin mixture obtained in the dimerization of propene (dipropene), heptenes, 2- or 3 methyl-1-hexene, octenes, 2-methylheptenes, 3-methylheptenes, 5-methyl-2-heptene, 6-methyl-2-heptene, 2-ethyl-1-hexene, the mixture of isomeric $C_8$-olefins obtained in the dimerization of butenes (dibutene), nonenes, 2- or 3-methyloctenes, the $C_9$-olefin mixture obtained in the trimerization of propene (tripropene), decenes, 2-ethyl-1-octene, dodecenes, the $C_{12}$-olefin mixture obtained in the tetramerization of propene or the trimerization of butenes (tetrapropene or tributene), tetradecenes, pentadecenes, hexadecenes, the $C_{16}$-olefin mixture obtained in the tetramerization of butenes (tetrabutene) and also olefin mixtures prepared by cooligomerization of olefins having different numbers of carbon atoms (for example, from 2 to 5 carbon atoms), optionally, after separation into fractions having an identical or similar chain length by distillation. The starting material may also include any mixture of the aforementioned.

For example, the octenes that are used in the production of nonyl alcohol, which is produced in large volumes for the manufacture of plasticiser ester, may be produced by the dimerisation of butenes employing a nickel containing catalyst, e.g. by the OCTOL™ or DIMERSOL™ processes, or dimerisation on a zeolite or other acidic catalyst. These processes yield substantially pure octenes. Alternatively, olefin mixtures averaging about eight carbon atoms may be obtained by the oligomerisation of olefin mixtures using acid catalysts such as phosphoric acid catalysts.

It is likewise possible to use olefins or olefin mixtures produced by Fischer-Tropsch synthesis and also olefins obtained by oligomerization of ethene or olefins obtainable via methathesis reactions. Exemplary starting materials for the preparation of the hydroformylation mixtures may be generally $C_8$-, $C_9$-, $C_{12}$-, $C_{15}$- or $C_{16}$-olefins and/or mixtures thereof.

Hydroformylation

The olefins are hydroformylated in manners well known in the art and their products may be utilized as starting materials for the hydrogenation process. Hydroformylation is a well-known process in which an olefin is reacted with carbon monoxide and hydrogen in the presence of a catalyst to form aldehydes and alcohols containing one carbon atom more than the feed olefin. This process has been operated commercially for many years and there have been two principal technology families used, one of which is known as the low pressure oxo process family and which generally involves the use as catalyst of an organometallic complex of rhodium with organophosphorous ligands for providing the necessary stability at the lower pressures and operates at pressures from 10 to 100 Bar. The second process family is known as the high or medium pressure process family and generally involves the use of an unmodified cobalt or rhodium based catalyst and typically operates at pressures from 100 to 350 Bar. Generally the low pressure processes are used for the hydroformylation of unbranched and terminal, primarily lower olefins such as ethylene, propylene and n-butenes, but also including n-hexene-1 and n-octene-1, or surfactant range Fischer-Tropsch olefin mixtures, whereas the high or medium pressure processes are primarily used for the hydroformylation of linear and/or branched higher olefins or mixtures such as those containing 5 or more carbon atoms. This process is widely used to produce what are known as "higher alcohols" or aldehydes or acids that are in the $C_6$ to $C_{15}$ range particularly the $C_9$ to $C_{13}$ range. Several embodiments disclosed herein are particularly applicable to the high pressure cobalt catalyzed hydroformylation process since the production of formate esters is particularly high when that technology is employed.

The hydroformylation typically uses a homogeneously dissolved catalyst complex, which may be based on cobalt or rhodium, and sometimes palladium. Ligands may be used to modify the catalyst complex, usually being phosphorous based, and tributylphosphine is typically known to be used with cobalt metal. With rhodium, the ligands are typically organophosphines, with triphenylphosphine (TPP) or the oxide variation thereof, or organophosphites.

Where cobalt catalyzed hydroformylation is used, the product is typically decobalted. In one embodiment, this is done by neutralising the active cobalt species $HCo(CO)_4$, with a base such as sodium hydroxide or carbonate in a decobalter. The decobalter conditions are such that the neutralization converts the hydrocobalt carbonyl to sodium cobalt carbonyl. Exemplary conditions are to use a stoichiometric excess of sodium hydroxide or carbonate above the amount needed for cobalt neutralization, an excess of up to 200% particularly from 100% to 180% is useful. The decobalter is typically operated at a temperature in the range 155-165° C. and it is preferred that sufficient carbon dioxide and/or carbonate is present in the decobalter to ensure the formation of sodium cobalt carbonyl and to also buffer the pH in the range 7.8 to 8.5. See, for example, WO 2006/122526.

Water may be present in the hydroformylation reactors. The injection of water reduces the formation of formate esters and heavy by products. In a class of embodiments, when used with multiple reactors, water should be injected into the first reactor, and may also be injected into the second and subsequent reactors. In a gas-lift reactor, the formation of a significant volume of a stagnant free water phase in the bottom may become an impediment or even an obstruction to the circulation of the reactor fluid. Gas-lift reactors from which any free water is continuously removed from the bottom have been described in WO 01/14297. In an embodiment, if there is no water removal capability, the quantity of water that is introduced should preferably not exceed or not exceed by more than 10 or 20% the solubility of the water in the reaction mixture, to avoid the formation of a stagnant free water phase in the reactor.

In several embodiments, 3 wt % or less, alternatively, 2 wt % or less of water based on the weight of olefin feed should be used in the first hydroformylation reactor(s), for example, a plurality of reactors connected in series, and typically from 1.0 wt % to 1.75 wt %, and alternatively, 1.5 wt % should be used. The weight of the olefin feed being the weight of unsaturated materials in the feed which is typically above 95 wt % of the feed and frequently about 99 wt % of the feed. Where water is injected into the second reactor, similar considerations may apply depending on the design of the reactor. Due to the different liquid composition in the second reactor, the water solubility may be different in this reactor, and typically a total of 2.5 wt % water may be present based on the olefin feed. These amounts of water apply readily in the production of $C_6$ to $C_{11}$ alcohols. They may however have to be reduced for the production of heavier alcohols because of the lower water solubility of their hydroformylation reaction mixtures.

The injection of water provides a significant improvement in plant utilization as well as carbon monoxide utilization. The water should be injected in a manner that ensures good mixing of the water with the reactants and also prevents large fluctuations in the olefin to water feed ratios.

Thus, in a class of embodiments, water may be injected into a fully operational reactor and when a loop reactor is used, it is preferred that the materials are circulating at a velocity of at least 0.6 meters/sec when the water is injected. Water and the olefins may be continuously introduced into the reactor at the desired water to olefin ratio.

Typically, hydroformylation may be carried out using rhodium or cobalt catalysts with or without additives to stabilize the complex, e.g. organic phosphines or phosphites. The temperatures and pressures can, depending on the catalyst or olefin, be varied within wide limits. An additional description of the hydroformylation of olefins may be found, for example, in J. Falbe, New Syntheses with Carbon Monoxide, Springer-Verlag, Heidelberg-New York, 1980, page 99 ff., and also in Kirk-Othmer, Encyclopedia of Chemical Technology, volume 17, 4th edition, John Wiley & Sons, pages 902 to 919 (1996).

In a class of embodiments, preference is given to using hydroformylation mixtures prepared from $C_8$-, $C_{12}$-olefins, or $C_8$-, $C_{12}$-olefin mixtures. However, embodiments disclosed herein may be used with any hydroformylated mixture known in the art. Additionally, the hydrocarbons (e.g., olefins and paraffins) may be separated off from the hydroformylation mixture prior to the hydrogenation.

Hydrogenation

In an embodiment, the hydrogenation of aldehydes occurs by means of a liquid phase in the presence of water and may be carried out using pelletized/shaped extrudates catalysts located in a fixed bed. These catalysts may include one or more metals of groups 1b, 2b, 6b, 7b and/or 8 of the Periodic Table, in particular, nickel, copper, chromium, and moly catalysts. Specific examples include without limitation copper chromite, nickel, sulphided nickel molybdenum, nickel molybdenum, sulphided cobalt molybdenum, cobalt molybdenum, and combinations thereof. It is possible to use catalysts on supports such as aluminum oxide, silicon oxide, titanium oxide, aluminosilicates or support-free catalysts.

In yet other embodiments, it is also possible to use catalysts without support materials. These catalysts generally include from about 0.2 to 30 wt % of nickel, from about 0.3 to 40 wt % of copper, and from about 18 to 40 wt % of chromium, based upon the total weight of catalyst. In an embodiment, the hydrogenation catalyst comprises CuCr which contains Cu, Cr, Ba, and, optionally, Si. The catalysts can further include up to 20% by mass of basic substances such as alkali metal or alkaline earth metal oxides or hydroxides, and also other inert or property-modifying materials in the same amounts, for example graphite. In many embodiments, the catalysts used do not contain any sulfur or sulfur compounds.

In an embodiment, supported catalysts may contain from 0.3 to 15% by weight of copper and from 0.3 to 15% by weight of nickel and also, as activators, from 0.05 to 3.5% by weight of chromium and from 0 to 1.6% by weight of an alkali metal. The support material may include aluminum oxide and/or silicon oxide.

In a class of embodiments, the catalysts are used in a form in which they offer a low flow resistance, e.g. in the form of granules, pellets, or shaped bodies such as tablets, cylinders, spheres, extrudates or rings. They are often activated prior to use by heating in a stream of hydrogen at, for example, from 140 to 250° C. if they are not reduced in the hydrogenation reactor. For example, a method of reduction by means of hydrogen in the presence of a liquid phase is described in DE 199 33 348.3.

Hydrogenation may be carried out in the homogeneous liquid phase in the presence of water, with the homogeneous liquid phase output from the reactor containing from 0.05 to 10% by weight, alternatively, from 0.5 to 8% by weight, and alternatively from 1 to 5% by weight, of water based upon the total weight of the output. The water contents are to be regarded as independent of consumption of water by chemical reactions and of discharge of water together with the offgas from the hydrogenation. In some embodiments, under the reaction conditions of the hydrogenation, the water is present mainly in the organic starting material/product phase and only a small proportion is present in the gas phase. In this case, little or no water is present in the gas phase and a further, liquid water phase is not present. The specific amount of water in the organic phase is determined by the solubility of water, the vapor pressure of water, and the phase ratio (gas to liquid) under the reaction conditions. The minimum amount of water necessary is that which is consumed in the hydrolysis of formic acid esters, acetals, ether aldehydes, aldol condensation products, and any other hydrolyzable substances.

Particularly with liquid phase hydrogenation, the hydrogenation reactors may be vertical tubes, provided with a jacket for temperature control and heat removal. They may be operated in upflow or in downflow mode. In the jacket, water or another suitable cooling medium such as an alkanol, preferably methanol, may be circulated using a pumparound system from which hot cooling medium may be withdrawn, and to which cold cooling medium may be supplied. Each reactor may be provided with a so-called conditioner, which is a heat exchanger one side of which is part of the cooling medium circulation, and which on the other side is for conditioning the reactor feed to the appropriate temperature before it passes to the reactor itself. Conditioning of the reactor feed is especially important when a reactor that is not a lead reactor contains relatively fresh and active catalyst, and therefore needs to be operated at start-of-run conditions, this typically requires a lower temperature. The upstream reactor on the other hand, may contain partially deactivated catalyst and therefore needs to be operating at mid-of-run or end-of-run conditions, which may require a higher temperature. Feed conditioning may therefore avoid a reactor feed that is too hot for an active catalyst to handle, and may therefore reduce the risk for temperature runaway.

In gas phase hydrogenation, the reactors may contain one of more fixed beds of catalyst, and cooler fresh or recycle hydrogen may be injected in the reactor, its feed or in between the catalyst beds in the reactor for temperature control.

The product from the hydroformylation step, typically after removal of the metal catalyst, may be routed directly to the subsequent hydrogenation step, or unreacted olefins may first be distilled away and optionally recycled, and the remainder of the stream may then be fed to hydrogenation, typically including formate esters, acetals and other heavies.

Also in the hydrogenation step, water is typically introduced, with the purpose to further promote the reduction of formic acid esters, acetals, ether aldehydes, aldol condensation products, and any other hydrolyzable substances.

Formate esters may thus also during hydrogenation be hydrolyzed and produce byproduct formic acid. Some hydrogenation catalysts are more resistant to the presence of formic acid as compared to others. Methanol may be formed as a byproduct from some of the reactions wherein formate esters are reacted away in the hydrogenation step. We have found that the formation of methanol during hydrogenation may depend on the type of hydrogenation catalyst, on the amount of water present, and on the hydrogenation conditions.

A reduction of the acetals in the hydrogenation step down to low levels is particularly important because any acetals left in the hydrogenation product may end up as heavies in the bottom byproduct from the alcohol distillation step which typically follows downstream. Some hydrogenation catalysts are better in the removal of acetals as compared to others.

The selection of a hydrogenation catalyst may thus be directed by several criteria in addition to its activity in aldehyde hydrogenation. For example, a sulphided bimetallic catalyst in the hydrogenation step of the alcohol process has good activity in converting formate esters and reducing acetals to very low levels, while withstanding formic acid and sulphur impurities in the hydrogenation feed.

If the starting material contains large amounts of hydrolyzable compounds, it may be necessary to add only part of the required water at the beginning in order to prevent formation of a second aqueous phase in the hydrogenation reactor. The other part is then fed in during the hydrogenation as a function of the water consumption. When using only one reactor, this may be carried out at one or more points on the reactor; when using a plurality of reactors connected in series, before the individual reactors. To prevent any aldehyde protected as hemiacetal or acetal from escaping hydrogenation, the output from the hydrogenation (in the case of a plurality of reactors, from the last reactor) may still contain water. The water content of the homogeneous liquid phase of the output from the reactor may be from 0.05 to 10 wt %, alternatively, from 0.5 to 8 wt %, based upon the total weight of the output.

Various process variants may be chosen. The hydrogenation process may be carried out adiabatically or virtually isothermally, i.e., with a temperature increase of less than 10° C., in one or more stages. In the latter case, all reactors, for example, tube reactors, may be operated adiabatically or virtually isothermally or one or more are operated adiabatically and the others are operated virtually isothermally. It is also possible for the aldehydes or aldehyde mixtures to be hydrogenated in the presence of water in a single pass or with product recirculation.

In a class of embodiments, the hydrogenation process may be carried out in concurrent in the trickle phase or preferably in the liquid phase in three-phase reactors, and the hydrogen is dispersed in the liquid aldehyde stream. For uniform liquid distribution, improved removal of heat of reaction, and a high space-time yield, the reactors are operated as high liquid throughputs of from 15 to 120 m$^3$, alternatively, from 25 to 80 m$^3$, per m$^2$ of cross section of the empty reactor an hour. If a reactor is operated isothermally and in a single pass, the space velocity over the catalyst may be from 0.1 to 10 h$^{-1}$.

In an embodiment, the hydrogenation of hydroformylation mixtures having from 8 to 17 carbon atoms, for example isononanal or tridecanal, preference is given to using a plurality of reactors connected in series. In this embodiment, the first reactor is operated in the recirculation mode and the subsequent reactors are operated in the recirculation mode or in a single pass. As a reactor operated in the recirculation mode, it is possible to use, for example, a shaft oven with a heat exchanger in an external circuit or a shell-and-tube reactor.

To minimize secondary reactions and thus to increase the alcohol yield, it is advantageous to limit the aldehyde concentration in the feed to the reactor. In a class of embodiments, in the hydrogenation of hydroformylation mixtures having from 8 to 17 carbon atoms, the aldehyde content in the reactor feed is from 1 to 35%, alternatively, from 5 to 25%. In the case of reactors operated in the recirculation mode, a concentration in the desired range may be set by means of the recirculation ratio (ratio of recirculated hydrogenation product to feed).

In a class of embodiments, hydrogenation processes may be carried out in a pressure range from 5 to 100 bar, alternatively, from 5 to 40 bar, and alternatively, from 10 to 25 bar. In a class of embodiments, hydrogenation processes may be carried out at temperatures in the range from 120 to 260° C., alternatively, from 140 to 190° C.

In a class of embodiments, the hydrogen necessary for the hydrogenation is used in pure form in only a small excess, so that little water goes into the gas phase and is carried out with the latter. In some embodiments, the amount of hydrogen fed into each reactor may be from 103 to 150% or less of the amount consumed by the reaction, and alternatively, from 103 to 120% or less. In other embodiments, the hydrogen consumed in the hydrogenation is replaced in an excess of from 3 to 50% or less, alternatively, from 3 to 20% or less, and alternatively, from 5 to 10% or less.

In an embodiment, in the first hydrogenation reaction, the aldehydes or aldehyde mixtures are hydrogenated fast to the corresponding alcohol, while the formation of acids is reduced. We believe that this beneficial effect is obtained by keeping the temperature in the first hydrogenation reactor limited to the specified maximum. This may be achieved by any of a series process features, such as a lower reactor inlet temperature or a partial recycle of the product of the first hydrogenation reactor, or of the hydrogenation product. Using partial recycle of a hydrogenation reactor product or the product of the hydrogenation section to the feed of the hydrogenation section has, in addition to its first benefit by dilution on lowering the reaction exotherm. While the aldehyde hydrogenation reaction rate is first order in aldehyde concentration, the acid formation via the Cannizzaro reaction involves two aldehyde molecules and is therefore second order in aldehyde concentration. The positive effect of the dilution on reducing the acid formation rate via the Cannizzaro reaction may thus be much stronger than the negative effect on the aldehyde hydrogenation rate. The intermediate or product recycle brings further the additional advantage that the water solubility of the total hydrogenation feed is increased, such that any entrained or injected water more readily dissolves into the organic stream, thereby reducing the risk of exposing equipment and/or catalyst to a free water phase, which may possibly build up inside the equipment, especially in a reactor operating in upflow mode, and which may cause corrosion of the equipment. An exemplary hydrogenation section intermediate recycle operation is described in more detail in, for example, U.S. Pat. No. 4,877,358.

The amount of water present during hydrogenation is an important factor in the hydrogenation process. For example, a higher water presence may tend to increase the formation rate of acids from aldehydes, which is a disadvantage. Conversely, a higher water concentration favorably affects the equilibrium between acids and their esters, in this case both heavy di-alkyl esters and methyl esters. In several embodiments, at least 1 wt % of water, alternatively, at least 2 wt % of water in the feed to the first hydrogenation reactor is utilized, and alternatively, at least 3 wt %, based on the total weight of liquid hydrogenation feed. In other embodiments, from 1 wt % to 5 wt % of water, alternatively, from 2 wt % to 4 wt % of water, based upon the total weight of the hydrogenation feed may be used. These balanced amounts of water keep the acid and/or alcohol (i.e., methanol) production and other unwanted compounds under control or at least mitigated, and also reduces the appearance of esters thereof in the product of the first hydrogenation reactor, and further downstream in the hydrogenation product.

In embodiments, wherein several reactors are utilized, for example, a plurality of reactors connected in series, water may be introduced or be present in the initial feed and/or may be introduced at any intermittent point in the reactor scheme. In these embodiments, the water concentrations referenced above may be the concentration at any one point or the total concentration of water of the aggregation of several points of injection. For example and illustration purposes only, 1 wt % may be fed at the initial feed and an additional 2 wt % of water may be introduced between the first and second, and/or the second and third reactors, for three reactors connected in series. In this embodiment, it may be said that 3 wt % water is fed into the hydrogenation process.

In several embodiments wherein the hydrogenation feed contains formates (e.g., up to 10 wt % based upon the total weight of the feed or up to 15 wt % based upon the total weight of the feed), the formates in the presence of water may decompose to methanol and formic acid, and subsequently, to carbon dioxide and hydrogen. Maintaining the ideal concentration of water is important because having too little water will promote methanol production and is undesirable as it promotes the production of waste water via the distillation section that will require appropriate disposal. Conversely, generating hydrogen is advantageous as it may be used in the hydrogenation process (which generally prefers a hydrogen excess) which in turn will require less hydrogen from an external source. Thus, this in-situ generation of hydrogen will allow the hydrogenation process to utilize a lower hydrogen feed flow.

In a class of embodiments, in the hydrogenation process, formates may decompose in the presence of water producing hydrogen. The water present may be in the amount as described above. This hydrogen may then be utilized in the hydrogenation process of converting aldehydes or aldehyde mixtures to alcohols. Thus, when hydrogen is produced from the decomposition of formates, close to or less than the stoichiometric amount of hydrogen can be fed into the reactor. As used herein, "close to" refers to within 80% of the stoichiometric amount of hydrogen, alternatively, within 85% of the stoichiometric amount of hydrogen, alternatively, within 90% of the stoichiometric amount of hydrogen, alternatively, within 95% of the stoichiometric amount of hydrogen, and, alternatively, within 99% of the stoichiometric amount of hydrogen. In alternative embodiments, "close to" refers to within ±20% of the total stoichiometric amount of hydrogen, alternatively, within ±15% of the total stoichiometric amount of hydrogen, alternatively, within ±10% of the total stoichiometric amount of hydrogen, alternatively, within ±5% of the total stoichiometric amount of hydrogen, and, alternatively, within ±1% of the total stoichiometric amount of hydrogen, required to conduct the hydrogenation process.

In several embodiments disclosed herein, the aldehyde to alcohol conversion rate may be 90.0% or greater, alternatively, 95. % or greater, alternatively, 98.5% or greater, alternatively, 99.0% or greater; and, alternatively, 99.5% or greater, after undergoing hydrogenation in one more reactors or after undergoing one or more hydrogenation steps.

In other embodiments, a second hydrogenation reactor downstream of and connected in series with the first hydrogenation reactor is used. The second hydrogenation reactor may be loaded with a hydrogenation catalyst of the same or different type as in the first hydrogenation reactor. The second hydrogenation reactor may operate at a higher temperature than the first hydrogenation reactor, preferably using a temperature of at least 180° C., more preferably in the range of from 190 to 210° C., and typically at around 200° C. The higher temperature in the back end of the hydrogenation step brings the advantage of reducing the presence of acids, methyl esters, and/or of heavier di-alkyl mono-esters in the product of the hydrogenation step. This reduces the loss of valuable molecules by esterification in the bottom of any of the downstream distillation towers, and the loss of these heavier ester molecules with the heavy by product from such distillation. It also reduces the methyl ester content in the alcohol product after distillation.

In an embodiment, the first hydrogenation reactor may have a pressure of at least 55 barg, alternatively at least 60 barg. These pressures generally provide sufficient partial pressure of hydrogen to drive the hydrogen consuming reactions. Alternatively, the reactor may have a pressure of at least 120 barg, and alternatively, at least 125 barg. At the higher pressure, the acidity is reduced, and thereby the loss of valuable molecules as di-alkyl esters in the heavy byproduct from distillation. A higher pressure however may lead to a higher methanol make from the formate esters in the hydrogenation feed, which may lead to a higher methyl ester content in the hydrogenation product, and thus, in the product alcohol. In some embodiments, the pressure is not more than 130 barg. Further pressure increases were found to have only negligible effects, while they further increase the investment cost of the equipment.

In yet another embodiment and a liquid phase hydrogenation process, the product from the first hydrogenation reactor then passes in a line to the second hydrogenation reactor and it is preferred that the line be provided with an inlet for the injection of water and a mixer whereby the water and the product may be mixed to ensure that the water is dissolved and/or entrained in the product. From 1 to 2 wt % of water based on the weight of the product may be injected into the reactor. The mixture then passes to the second hydrogenation reactor where it passes through the catalyst bed at a temperature of 180 to 210° C. in the presence of hydrogen. The product then flows downwardly in the second reactor.

Downstream Processing and Products

Following the last hydrogenation reactor the product passes to a high pressure separator in which unreacted hydrogen may be flashed off and, if desired, recycled to the hydroformylation reactors as is described in WO 2005/058787. It is also possible to recycle some or all of this unreacted hydrogen to the hydrogenation reactors. In this embodiment only a portion of the unreacted hydrogen is passed to the hydroformylation reactors.

The product of hydrogenation process generally comprises a mixture of the desired alcohols, olefins, paraffins, ether alcohols, ether aldehydes, acetals and traces of aldehydes and formates together with dissolved carbon dioxide and dissolved hydrogen and water, and aliphatic esters of carboxylic acids. The product may then be purified firstly through a coalescer to remove water, followed by fractional distillation to separate the $C_6$ to $C_{17}$ alcohol from the lower boiling fraction of the mixture and a second distillation to separate the alcohol from the higher boiling fraction. Water and any methanol or other lower alcohols typically will be separated with the lower boiling fraction, and may settle out as a separate phase in the tower overhead system, from where they can be discarded or taken for further use. The presence of methanol may cause problems requiring special disposal techniques.

In several embodiments, the hydrogenation product undergoes a distillation step. This may be carried out at atmospheric pressure or under reduced pressure. In the case of high-boiling alcohols, i.e., $C_8$-$C_{17}$ alcohols, distillation under reduced pressure may be practiced.

In some embodiments, processes for producing alcohols may comprise the hydroformylation of lower carbon number olefins, such as ethylene, propylene and butenes to the corresponding aldehyde or aldehyde mixtures containing one more carbon number than the starting olefin or olefins. These aldehydes, or mixtures thereof, are then subjected to aldolisation to produce condensation products, typically higher aldehydes containing an extra carbon-carbon double bond, often referred to as enals. These enals or enal mixtures may be hydrogenated to the corresponding saturated aldehydes or aldehyde mixtures, or directly to the corresponding alcohols or alcohol mixtures. Examples of products produced by such processes are 2-methylpentanol, 2-ethylhexanol, 2,4-dimethylheptanol and 2-propylheptanol, but other alcohols and alcohol mixtures produced in this way are also known.

Other exemplary products of several embodiments disclosed herein include alcohols such as hexanols, heptanols, octanols, nonanols, decanols, dodecanols, tridecanols, and etc. ($C_6$, $C_7$, $C_8$, $C_9$, $C_{10}$, $C_{12}$, $C_{13}$, $C_{14}$, $C_{15}$, $C_{16}$, and $C_{17}$ alcohols) either as pure compounds, mixtures, mixtures of isomers, and combinations thereof.

Additionally, in some embodiments, downstream processes to produce organic compounds, such as plasticizers and detergents, are performed. Examples of downstream processes include esterification reaction between the product alcohol and phthalic acid (anhydride) to produce one or more plasticizers. Another example includes admixing the plasticizer and a polymer resin to produce a polymer composition.

EXAMPLES

It is to be understood that while the invention has been described in conjunction with the specific embodiments thereof, the foregoing description is intended to illustrate and not limit the scope of the invention. Other aspects, advantages and modifications will be apparent to those skilled in the art to which the invention pertains.

Therefore, the following examples are put forth so as to provide those skilled in the art with a complete disclosure and description and are not intended to limit the scope of that which the inventors regard as their invention.

Test Methods

Analytical Method for Carbonyl Number (CN No.)

The purpose of determining a carbonyl number (or also herein "CN No.") is to determine the carbonyl content of the different oxo and acid products. It is based upon the method disclosed in ASTM E411. In particular, the determination of the carbonyl number of oxo, hydro, and acid products may be conducted using colorimetry on a technicon continuous flow analyser. In general, the aldehydes contained in a sample are reacted with 2-4 dinitrophenylhydrazine. The hydrazone complex formed is extracted with isooctane, and the extract's absorbance is measured at a specific wavelength (for example, 340 nm). Following, the carbonyl number is calculated from a calibration curve, taking into account the sample weight, and is expressed in mg KOH/g of the sample.

Equipment used to perform the method typically includes a Technicon Auto Analyser II sampler, Technicon Auto Analyser II proportioning pump, Technicon Auto Analyser II manifold specially designed for carbonyl determination, Technicon Auto Analyser II S.C. Colorimeter equipped with a filter of 340 nm wavelength, Technicon recorder, an analytical balance, PC with appropriate software, volumetric flasks from 10 to 1000 ml, and pipettes.

Reagents used to perform the method typically includes:
Ethanol (absolute and carbonyl free);
Recrystallized 2-4 dinitrophenylhydrazine (DNPH). Reference: weigh 30 g of DNPH in a 21 distillation flask. Add 1 l absolute ethanol and reflux 3 hours. Cool the mixture, and filter the DNPH through a Buchner funnel. Dry the DNPH overnight in an oven at 70° C.;
DNPH solution. Dissolve 1.000 g recrystallized DNPH in 1.000 milliliter carbonyl free ethanol containing 10 ml concentrated HCl and 10 ml demineralized water;
Sodium bicarbonate solution (1% in distilled water);
Isooctane p.a. and carbonyl free (prepared by 15 refluxing at boiling point, followed by distillation over a short column, discarding the first 10% and last 10%);
Isooctane p.a. distilled+30% absolute ethanol. Prepare a 70% isooctane p.a. distilled/30% absolute ethanol mixture (volume %);
Isooctane p.a. distilled+2.5% absolute ethanol. Prepare a 97.5% isooctane p.a. distilled/2.5% absolute ethanol mixture (volume %);
Isooctanone Merck art 820926;
Hydrochloric acid conc. p.a.; and
Distilled water.

The procedure utilizes the following: ASTM E411, DAM 11-82 (Long Method), DAM 12-82 (Short Method), and DAM 7-83 (Technicon method).

Standards Preparation

The carbonyl determination is based on a calibration curve, so it is necessary to prepare standards. All calculations are based on 25 ml volume for the standards and the samples. If the carbonyl content is high, take into account the supplementary dilutions.

Stock solutions: preparation:
Prepare 2 stock solutions, of respectively around 10 and 5 mg KOH isooctanone (MW=128.22) in 25 ml isooctane.
Stock standard solution 10 mg KOH in 25 ml (Solution A).
Accurately weigh about 0.4570 g isooctanone and dissolve it in a 500 ml volumetric flask, with isooctane p.a. distilled. Record the weight and calculate the actual amount of mg KOH/25 ml.
Stock standard solution 5 mg KOH in 25 ml isooctane (Solution B).
Same procedure as for Solution A but weigh 0.2285 g of isooctanone.
Standards (target for final volume of 500 ml)
Standard I: Stock A diluted 5 times=2.00 mg KOH in 25 ml.
Standard II: Stock A diluted 10 times=1.00 mg KOH in 25 ml.
Standard III: Stock A diluted 12.5 times=0.80 mg KOH in 25 ml.
Standard IV: Stock B diluted 10 times=0.50 mg KOH in 25 ml.
Standard V: Stock B diluted 20 times=0.25 mg KOH in 25 ml.
Standard VI: Stock B diluted 50 times=0.10 mg KOH in 25 ml.

Preparation of Samples

The samples have to be weighed in 25 ml volumetric flasks. In the alternative, one may dilute the samples in a way to be in the middle of the calibration curve (carbonyl between 0.80 and 0.50 mg KOH/25 ml).

Weigh the sample in a 25 ml volumetric flask and add isooctane to the final volume. Shake the sample to complete dissolution of the sample. If water is present, this solution may be cloudy, to avoid this add some ml ethanol p.a. to the isooctane solution until the mixture is clear.

Recommended weight and dilutions may be found in Table 1.

TABLE 1

| Carbonyl # | Weight (g) | Vol. Flask (ml) | 2nd dilution | Dilution Factor |
|---|---|---|---|---|
| 300 | 0.1500 | 100 | 10 | 40 |
| 200 | 0.1500 | 100 | 10 | 40 |
| 100-75 | 0.0500 | 100 | — | 4 |
| 50 | 0.0700 | 100 | — | 4 |
| 25 | 0.1000 | 100 | — | 4 |
| 10-5 | 0.1200 | 25 | — | 1 |
| 2-1 | 0.6000 | 25 | — | 1 |
| <1 | 1.5000 | 25 | — | 1 |

*Before weighing high carbonyl samples (i.e., above 100 mg KOH/g) place a small quantity of isooctane in the volumetric flask, to avoid a possible oxidation of the sample.
**Note that all the glassware has to be washed with isooctane and never with acetone.

Preparation of QC Sample

Dose 6 ml stock B solution in a total of 100 ml iso-octane. This should yield a QC of 0.3 mg KOH/25 ml.

Running the Technicon Analyser

The sample, diluted in isooctane will be treated with dinitrophenylhidazine in the presence of HCl. The aldehydes react to form hydrazones. The reaction takes place in a mixer at 65° C. The excess HCl is removed by washing with the bicarbonate solution. The hydrazone that has been formed is analysed colorimetrically at 340 nm. Accordingly, proceed according to the following.

Put all organic reactant tubes in absolute ethanol and the bicarbonate tube in water for a period of 10 minutes.
Place the bicarbonate tube in air for 10 minutes.
Place the DNPH pipe in the DNPH reactant solution, the 30% ethanol/70% isooctane tube in its solution and the 2.5% ethanol/97.5% isooctane in its solution for 18 min.
Place the bicarbonate tube in the bicarbonate solution for 30 min.
Observe the stability of the baseline. Take the necessary actions and if needed rinse the colorimeter with ethanol.
Set the recorder pen on the 5% scale on the recorder paper with the baseline adjustment button of the colorimeter.
Start on the PC the carbonyl tab page and start the process by pushing the start button.
On the auto sampler, place 1 cup containing the highest standard, a second cup filled with isooctane, then all the standards in decreasing order and finally one cup of isooctane.
After about 20 min the first peak appears on the recorder. Adjust its maximum to about 95% of the recorder scale with the "standard calibration" potentiometer of the colorimeter. After this adjustment, don't change any settings during the measurements. Place the QC samples and the unknown samples on the auto sampler. Each series ends by a cup of isooctane.

Manual Calculation

Trace the baseline and measure the peak heights.

Plot the peak heights of the standards versus the carbonyl content and carry out a linear regression to obtain the calibration curve. Determine the correlation factor r of the regression. The target for r is a minimum of 0.9975.

Calculate the carbonyl content of each sample, taking into account the weight and the different dilutions.

mgKOH/g in sample=dilution factor*(mgKOH in 25 ml/sample weight)

Reject all peaks lower than the lowest standard.

Analytical Method for SAP Number

The method directed to the saponification number or, alternatively, herein "SAP number" or "SAP No." is intended to determine the formate ester content in oxo process samples such as oxo product, hydroproduct, alcohol, and heavy fraction (HOF). The result gives the "raw" cold sap number that includes the free acids already present in the sample and the formate esters. Thus, to determine the "net" amount of formate ester, known as the "net cold sap number", a free acid titration is also required and will have to be subtracted from the "raw" cold sap number.

The saponification number is the amount of KOH expressed in milligrams necessary to saponify the formate esters in one gram of sample. The sample is reacted with an excess of KOH 0.1N at room temperature for 30 minutes. The excess KOH is than back titrated with HCl 0.1N by potentiometry.

Equipment used to perform the method typically includes a:

Metrohm titroprocessor 672;
Metrohm control unit 657;
Metrohm Dosimat 655 with burette 50.00 ml;
Metrohm Platinum Electrode 6.0302.110;
Metrohm Ag/AgCl reference electrode 6.0729.110;
Metrohm Separate pH glass electrode 6.0130.100;
An Analytical Balance Sartorius up to 0.0001 g; and
Titration vessel.

Reagents used to perform the method typically includes a:

Titration solvent isopropanol p.a.;
0.1 N Potassium hydroxide solution in ethanol (dilute titrisol Merck ref 9921 with Ethanol p.a. to 1000.0 ml);
0.1000 N Hydrochloric acid in distilled water (dilute Merck titrisol ref. 9973 with distilled water to 1000.0 ml); and
Heptylformate from Aldrich 99+% purity (ref nmb W255-203) as a Quality Control sample (QC with theoretical value=389 mg KOH/g at 100% purity).

Titration Procedure

The recommended weights of the samples (gram) is a function of their expected cold sap level in order to have good titration volume. They appear in Table 2 below.

TABLE 2

| Expected saponification number (mg KOH/g) | Weight (g) |
| --- | --- |
| 390 | 0.12 |
| 200 | 0.25 |
| 100 | 0.50 |
| 50 | 1.00 |
| 10 | 5.00 |
| 1 | 10.00 |
| <1 | 20.00 |

Preparation 3 Blanco's:

add 20.00 ml KOH 0.1000 N in Ethanol, add 100 ml isopropanol and titrate with HCl 0.1000 N in H2O;

Stir efficiently but not vigorously to avoid air bubbles to be entrained around the electrodes;

The "blanc value" is calculated as the average of the 3 titrations;

Rinse the electrodes after each titration; and

The blancs should titrate with a maximum deviation of +/−0.05 ml.

Start the series of analyses with 2 QC samples, which have to be treated in the same way as process samples. If the results of the QC samples differ more than 2 sigma from their mean, check the electrodes (clean or replace them) and verify all titration parameters.

Weigh the samples and introduce their weights and id number in the titroprocessor.

Immediately, after weighing, add 10 ml of IPA p.a. while simultaneously rinsing the inner side of the beaker. This manipulation prevents potential air oxidation of aldehydes to free acidity in particular when analysing samples with a high carbonyl numbers like hydrofeeds.

After all samples have been weighed, draw a report of the weights and check the print out.

Start the automatic titration.

100 ml isopropanol pro analyses and 20.00 ml KOH 0.1000N will automatically be added by the titrator to each sample in such a sequence that each sample will react 10 minutes with stirring and another 20 min without stirring at ambient temperature before the titration with HCl 0.1000 N starts.

The cold saponification number is calculated from the EP nearest to 0 mV. The following formula is used to calculate the cold sap number of a sample:

Cold saponification number=(ml blanc−ml titrate)*5.61/sample weight ml blanc=ml HCl 0.1000N needed to titrate 20.00 ml KOH 0.1000N ml titrate=ml HCl 0.1000N needed to titrate the excess of KOH after 30 min saponification of the formate esters in the sample.

5.61 as the mgKOH equivalent to 1.00 ml KOH. 0.1000 N

The result is expressed in mg KOH/g of sample

Figure 3:
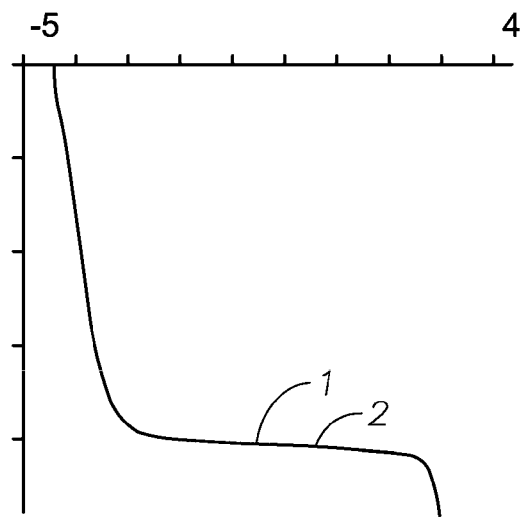
FIG. 3 is typical titration curve for a blanco sample. See SAP number below for a detailed explanation.
Figure 4:
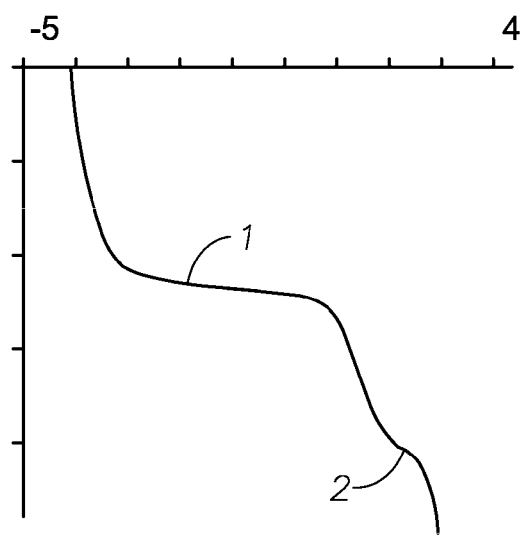
FIG. 4 is typical titration curve for a Quality Control sample (QC). See SAP number below for a detailed explanation.

FIGS. 3 and 4 show typical titration curves for the blanco and QC samples. In these examples, EP1 is selected for the calculation of the cold sap number. Embodiments disclosed herein may have net cold sap numbers from 10 to 50 mg KOH/g (in the hydroformylation product), alternatively, a net cold sap number of about 48 mg KOH/g (in the hydroformylation product).

Example 1

In a series of packed-bed hydrogenation reactors, formate conversion, aldehyde hydrogenation, and hydrogen consumption were monitored. The data indicate that $H_2$ from formate decomposition may be used to reduce the $H_2$/aldehyde feed ratio; thus, the hydrogen from an external reactor or reaction source may be reduced. The hydrogenation off-gas of the unit had a high $CO_2$ content which is further indication of the decomposition of formates into $CO_2$ and $H_2$. The following conditions and measurements were employed and observed.

TABLE 3

| Hydrogenation Catalyst | CuCr | CuCr |
|---|---|---|
| Alcohol | C10OH | C9OH |
| H2O | >1 wt % | >1 wt % |
| Reactor operating temperature | 140-200 | 140-200 |
| Reactor pressure | 40-60 | 40-60 |
| Mol ratio H2 Feed/aldehyde feed | 0.99 | 1.08 |
| Mol ratio H2 from formate/aldehyde feed | 0.20 | 0.18 |
| CN No. of feed | 123 | 140 |
| CN No. of product | 3.9 | 4.8 |
| SAP No. of feed | 30 | 28 |
| SAP No. of product | 4.2 | 2.7 |
| CO2 in offgas | 16 | 20 |
| VVH | 5 | 4 |

FIG. 1 represents data from this hydrogenation process. In the hydrogenation of aldehydes formed by the hydroformylation of olefins, 1 mol of hydrogen is needed for the hydrogenation of 1 mol of aldehyde, which is equivalent to a mol ratio $H_2$/aldehyde=1. Generally, an excess of $H_2$ is used for the hydrogenation reaction which is equivalent to a mol ratio higher than 1. FIG. 1 shows that the unit can run the hydrogen feed excess close to zero while using the hydrogen generated by formate decomposition.

In several classes of embodiments disclosed herein, formates may generally create a hydrogen excess of from 10%-100%, alternatively, 10%-50%, alternatively, 10-40%, and, alternatively, 30%-50%, based upon the total amount of hydrogen required to hydrogenate an aldehyde mixture to alcohols.

Example 2

The pilot plant hydrogenation reactor consisted of 4 tubular reactors of 120 ml each, lined up in series and operated in down flow mode. Hydroformylation (oxo) product was fed by means of a metering pump to the inlet of the first tube. The feed flow was controlled and measured with a mass flow controller. Water was mixed with the feed by a second metering pump. No hydrogen was fed to the reactor bundle. The reactors were positioned in a temperature controlled fluidized sand bath and therefore heated isothermically. Pressure was controlled at the outlet of the reactor bundle by means of a back pressure regulator. Gas and liquid were separated after cooling and depressurization in a gas/liquid separator. The outlet gas was measured with a dry gas meter and analysed for $H_2$, CO, $CO_2$. The product was collected, weighed and analysed. Analyses include: 1) Gas Chromatography for LOF (light Oxo Fraction), A/A/F (sum of aldehydes, alcohol, formate ester), ethers, etheralcohol, acetals and heaviers; 2) carbonyl analyses by UV (DNPH based); 3) acid number by titration; 4) raw cold sap number for formate ester+acid content. Operating conditions and results are reported below.

TABLE 4

| Catalyst | CuCr GR22 RS |
|---|---|
| Catalyst volume total | 458.4 ml |
| Feed type | $C_{10}$ Oxo Product |
| Temperature | 180° C. |
| Pressure | 8 barg |
| Feed Flow In | 1421 ml/h |
| Fresh $H_2$ In | 0.00 nl/h |
| Vvh | 3.1 |
| Product Flow Out | 1424 ml/h |
| Gas Flow Out | 18 nl/h |
| Feed Composition: | |
| LOF | 13.66 wt % |
| A/A/F | 69.20 wt % |
| Ethers | 2.98 wt % |
| Ether Alcohol | 10.01 wt % |
| Acetals | 4.13 wt % |
| Heavies | 0.00 wt % |
| Feed Carbonyl No. | 71.00 mg KOH/g |
| Feed Acid No. | 0.20 mgKOH/g |
| Feed Total Cold Sap No. | 48.00 mg KOH/g |
| Product Composition: | |
| LOF | 13.01 wt % |
| Aldehydes | 71.13 wt % |
| Ethers | 3.22 wt % |
| Ether Alcohol | 10.23 wt % |
| Acetals | 2.40 wt % |
| Heavies | 0.00 wt % |
| Product Carbonyl No. | 35.00 mg KOH/g |
| Product Acid No. | 3.40 mg KOH/g |
| Product Raw Cold Sap No. | 11.30 mg KOH/g |
| Off-gas Composition: | |
| $CO_2$ | 87.58 vol % |
| H2 | 12.02 vol % |
| CO | 0.40 vol % |
| Organics | 0.00 vol % |
| Material Balance: | |
| Formutes Converted | 1.016 mol/h |
| Hydrogen Purged | 0.097 mol/h |
| Aldehydes Converted | 0.912 mols/h |
| Mol Balance On Formates Converted | 99.3% |

Example 2 demonstrates that the formates conversion will follow the reaction routes (I) and (II) as shown in the BACKGROUND and generate hydrogen from the decomposition of formates which is available to be utilized in the aldehyde hydrogenation process.

Example 3

In a third set of experiments, the formation of methanol during hydrogenation of a $C_9$ hydrofeed was followed as function of temperature, water addition, and pressure. The unit lay-out was identical as explained in Example 2. The data are summarized in Table 5 below.

TABLE 5

| | Pressure, barg | | | | | | | | | | | | |
|---|---|---|---|---|---|---|---|---|---|---|---|---|---|
| | 55 | 55 | 56 | 57 | 56 | 57 | 58 | 57 | 56 | 56 | 57 | 135 | 135 |
| Temp, °C. | 170 | 170 | 170 | 170 | 170 | 190 | 190 | 190 | 190 | 190 | 190 | 190 | 200 |
| water inlet, vol % on feed | 1.9 | 1.85 | 2.03 | 2.31 | 1.89 | 1.63 | 2.67 | 3.57 | 1.91 | 1.8 | 1.81 | 1.94 | 1.93 |
| water to mid, vol % on feed | 0 | 0 | 0 | 0 | 0 | 0 | 0 | 0 | 1.92 | 1.8 | 1.81 | 1.94 | 1.93 |
| Total water, wt % on feed | 2.28 | 2.22 | 2.43 | 2.77 | 2.26 | 1.95 | 3.20 | 4.28 | 2.29 | 2.16 | 2.17 | 2.32 | 2.31 |
| Feed composition, wt % | | | | | | | | | | | | | |
| LOF | 1.56 | 1.56 | 11.51 | 11.51 | 11.51 | 1.56 | 1.56 | 1.56 | 1.56 | 1.56 | 1.56 | 8.78 | 8.78 |
| Alcohol | 56.86 | 56.86 | 79.72 | 79.72 | 79.72 | 56.86 | 56.86 | 56.86 | 56.86 | 56.86 | 56.86 | 61.43 | 61.43 |
| Ether | 1.41 | 1.41 | 0.94 | 0.94 | 0.94 | 1.41 | 1.41 | 1.41 | 1.41 | 1.41 | 1.41 | 0.79 | 0.79 |
| Eyher alcohol | 8.12 | 8.12 | 5.13 | 5.13 | 5.13 | 8.12 | 8.12 | 8.12 | 8.12 | 8.12 | 8.12 | 3.99 | 3.99 |
| Acetal | 28.48 | 28.48 | 2.51 | 2.51 | 2.51 | 28.48 | 28.48 | 28.48 | 28.48 | 28.48 | 28.48 | 22.25 | 22.25 |
| heavies | 3.56 | 3.56 | 0.16 | 0.16 | 0.16 | 3.56 | 3.56 | 3.56 | 3.56 | 3.56 | 3.56 | 2.76 | 2.76 |
| Carbonyl mgKOH/g | 82.20 | 82.20 | 86.40 | 86.40 | 86.40 | 82.20 | 82.20 | 82.20 | 82.20 | 82.20 | 82.20 | 170 | 170 |
| Cold sap mgKOH/g | 38.50 | 38.50 | 35.18 | 35.18 | 35.18 | 38.50 | 38.50 | 38.50 | 38.50 | 38.50 | 38.50 | 36.02 | 36.02 |
| % water/total hydrolyzable | 91.77 | 89.35 | 196.3 | 223.4 | 182.8 | 78.73 | 129 | 172.4 | 92.25 | 86.94 | 87.42 | 109.2 | 108.6 |
| Product comp, wt % | | | | | | | | | | | | | |
| methanol | 0.14 | 0.24 | 0.11 | 0.11 | 0.11 | 0.44 | 0.25 | 0.17 | 0.23 | 0.27 | 0.28 | 0.52 | 0.53 |
| LOF | 1.47 | 1.41 | 11.19 | 11.35 | 11.57 | 1.53 | 1.49 | 1.46 | 1.5 | 1.57 | 1.53 | 8.32 | 9.02 |
| Alcohol | 79.85 | 77.75 | 81.82 | 81.48 | 80.99 | 83.13 | 83.68 | 84.83 | 84.16 | 84.86 | 83.85 | 83.53 | 83.41 |
| Ether | 1.09 | 1.63 | 0.88 | 0.91 | 0.93 | 1.69 | 1.67 | 1.59 | 1.62 | 1.57 | 1.62 | 1.19 | 1.13 |
| Eyher alcohol | 8.72 | 8.48 | 5.1 | 5.15 | 5.26 | 8.75 | 9.21 | 9.63 | 9.49 | 9.26 | 9.89 | 5.02 | 4.6 |
| Acetal | 7.43 | 8.95 | 0.82 | 0.92 | 1.04 | 3.76 | 3 | 1.93 | 2.47 | 2.04 | 2.33 | 1.16 | 1.07 |
| heavies | 1.3 | 1.53 | 0.08 | 0.08 | 0.1 | 0.7 | 0.7 | 0.39 | 0.53 | 0.42 | 0.5 | 0.26 | 0.23 |
| Carbonyl mgKOH/g | 11 | 12.6 | 1.49 | 1.37 | 1.53 | 4.99 | 4.74 | 2.64 | 2.7 | 2.2 | 2.3 | 0.8 | 0.64 |
| Cold sap mgKOH/g | 2.55 | 2.63 | 0.49 | 0.34 | 0.64 | 1.61 | 0.54 | 0.4 | 1.24 | 1.62 | 0.66 | 0.05 | 0 |
| % methanol/formates | 6.375 | 10.93 | 5.482 | 5.482 | 5.482 | 20.04 | 11.38 | 7.741 | 10.47 | 12.29 | 12.75 | 25.31 | 25.8 |

Figure 2:
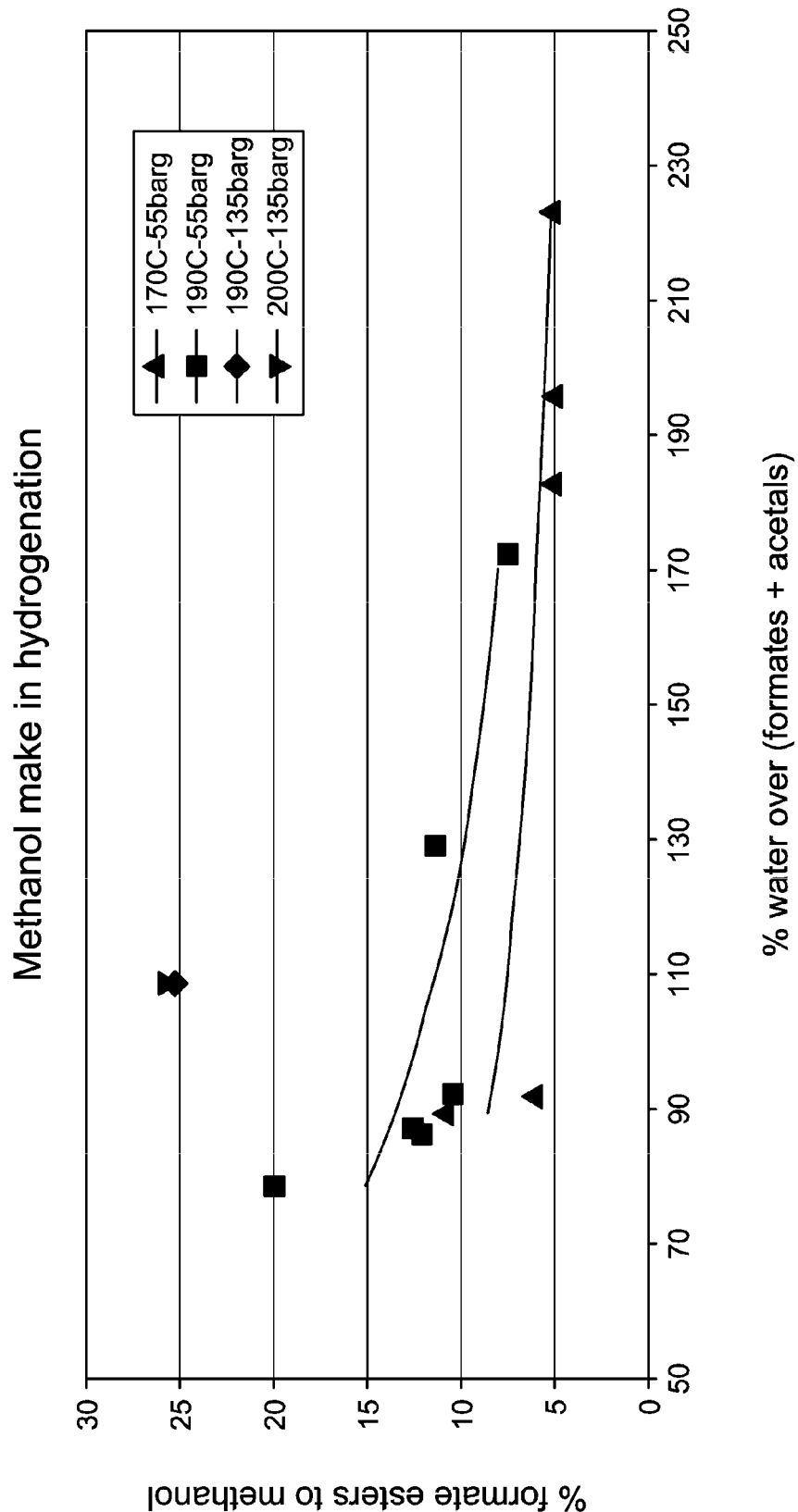
FIG. 2 shows a graph following the decomposition of formates into methanol during a hydrogenation process.

FIG. 2 illustrates that insufficient water (<100% over the sum of hydrolyzable formates and acetals), higher temperature, and higher operating pressure increase the fraction of formates that are decomposed to methanol by the undesired reaction as shown in reaction route (III). (See BACKGROUND.)

The phrases, unless otherwise specified, "consists essentially of" and "consisting essentially of" do not exclude the presence of other steps, elements, or materials, whether or not, specifically mentioned in this specification, so long as such steps, elements, or materials, do not affect the basic and novel characteristics of the invention, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc. are herein fully incorporated by reference for all jurisdictions in which such incorporation is permitted and to the extent such disclosure is consistent with the description of the present invention.

While the invention has been described with respect to a number of embodiments and examples, those skilled in the art, having benefit of this disclosure, will appreciate that other embodiments can be devised which do not depart from the scope and spirit of the invention as disclosed herein.

What is claimed is:

1. A process for the production of a $C_6$-$C_{15}$ alcohol mixture comprising the steps of:
   hydroformylating an olefin mixture comprising at least one branched $C_5$-$C_{14}$ olefin to form a hydroformylation product comprising aldehydes and formates;
   feeding the hydroformylation product into a hydrogenation step comprising contacting, in at least one first hydrogenation reactor, at least one catalyst selected from the group consisting of at least one of copper chromite, nickel, sulphided nickel molybdenum, nickel molybdenum, sulphided cobalt molybdenum, cobalt molybdenum, and combinations thereof, at least 1 wt % water, based upon the total weight of the feed, hydrogen, and the hydroformylation product to convert the hydroformylation product to a $C_6$-$C_{15}$ alcohol mixture;
   wherein, the hydrogen is supplied from the decomposition of the formates and at least one source external to the at least one first hydrogenation reactor, and wherein at least 5% or greater of the total stoichiometric amount of hydrogen necessary to hydrogenate the aldehydes is supplied from the decomposition of the formates and 100% or less than 100% of the total stoichiometric amount of hydrogen necessary to hydrogenate the aldehydes is supplied from the at least one source external.

2. The process according to claim 1, wherein the temperature in the first hydrogenation reactor is in the range from 140 to 250° C.

3. The process according to claim 1, comprising at least one second hydrogenation reactor connected downstream of the first hydrogenation reactor, wherein the temperature in the second hydrogenation reactor is in the range from 160 to 250° C.

4. The process according to claim 1, wherein the amount of water present is from 1 to 5% by weight, based upon the total weight of the feed, in one or more reactors.

5. The process according to claim 1, wherein the pressure in the hydrogenation section is from 20-140 barg.

6. The process according to claim 1, wherein the hydroformylation product has a net cold sap number from 10 to 50 mg KOH/g.

7. The process according to claim 1, wherein the hydroformylation product has a net cold sap number of about 48 mg KOH/g.

8. The process according to claim 1, wherein the at least one liquid hydrogenation feed comprises 15 wt % or less of the formates based upon the total weight of the feed.

9. The process according to claim 1, wherein the at least one liquid hydrogenation feed comprises from 1-60 wt % aldehydes based upon the total weight of the feed.

10. The process according to claim 1, wherein the at least one catalyst is CuCr comprising Cu, Cr, Ba, and, optionally, Si.

11. The process according to claim 1, wherein the at least one catalyst is supported.

12. The process according to claim 1, wherein at least 10% or greater of the total stoichiometric amount of hydrogen necessary to hydrogenate the aldehydes is supplied from the decomposition of the formates.

13. The process according to claim 1, wherein at least 15% or greater of the total stoichiometric amount of hydrogen necessary to hydrogenate the aldehydes is supplied from the decomposition of the formates.

14. The process according to claim 1, wherein at least 25% or greater of the total stoichiometric amount of hydrogen necessary to hydrogenate the aldehydes is supplied from the decomposition of the formates.

15. The process according to claim 1, wherein at least 30% or greater of the total stoichiometric amount of hydrogen necessary to hydrogenate the aldehydes is supplied from the decomposition of the formates.

16. The process according to claim 1, wherein the aldehyde to alcohol conversion rate is 90.0% or greater after undergoing one or more hydrogenation steps.

17. The process according to claim 1, wherein the aldehyde to alcohol conversion rate is 99.0% or greater after undergoing one or more hydrogenation steps.

18. The process according to claim 1, wherein the aldehyde to alcohol conversion rate is 99.5% or greater after undergoing one or more hydrogenation steps.

19. The process according to claim 1, wherein the hydrogen supplied from the decomposition of the formates and the at least one source external to the at least one first hydrogenation reactor is supplied in an excess of from 10-100% of the total stoichiometric amount of hydrogen necessary to hydrogenate the aldehydes.

20. The process according to claim 1, wherein the hydrogen supplied from the decomposition of the formates and the at least one source external to the at least one first hydrogenation reactor is supplied in an excess of from 10-50% of the total stoichiometric amount of hydrogen necessary to hydrogenate the aldehydes.

21. The process according to claim 1, wherein the hydrogen supplied from the decomposition of the formates and the at least one source external to the at least one first hydrogenation reactor is supplied in an excess of from 10-40% of the total stoichiometric amount of hydrogen necessary to hydrogenate the aldehydes.

22. The process according to claim 1, wherein the hydrogen supplied from the decomposition of the formates and the at least one source external to the at least one first hydrogenation reactor is supplied in an excess of from 30-50% of the total stoichiometric amount of hydrogen necessary to hydrogenate the aldehydes.

23. The process according to claim 1, further comprising esterifying the $C_6$-$C_{15}$ alcohol mixture with at least one acid or at least one anhydride to form at least one ester.

24. The process according to claim 23, wherein the at least one acid or the at least one anhydride is selected from the group consisting of at least one of benzoic acid, phthalic acid, adipic acid, trimellitic acid, cyclohexanoic acid, cyclohexanoic dibasic acid, pyromellitic acid, their corresponding anhydrides, and mixtures thereof.

* * * * *